US00PP20414P2

(12) United States Plant Patent
Bergman

(10) Patent No.: US PP20,414 P2
(45) Date of Patent: Oct. 13, 2009

(54) *HIBISCUS* PLANT NAMED 'SCARLET LOKE'

(50) Latin Name: *Hibiscus rosa-sinensis*
Varietal Denomination: Scarlet Loke

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 12/221,683

(22) Filed: Aug. 4, 2008

(51) Int. Cl.
*A01H 5/00* (2006.01)

(52) U.S. Cl. ..... Plt./257

(58) Field of Classification Search ..... Plt./257
See application file for complete search history.

*Primary Examiner*—Kent L Bell
(74) *Attorney, Agent, or Firm*—C. A. Whealy

(57) ABSTRACT

A new and distinct cultivar of *Hibiscus* plant named 'Scarlet Loke', characterized by its compact, upright, somewhat outwardly spreading and dense plant habit that is appropriate for container production; glossy dark green-colored leaves; uniform, freely and early flowering habit; large scarlet red-colored flowers; and good postproduction and garden performance.

1 Drawing Sheet

Botanical designation: *Hibiscus rosa-sinensis.*
Cultivar denomination: 'SCARLET LOKE'.

BACKGROUND OF THE INVENTION

The present invention relates to a new and distinct cultivar of *Hibiscus,* botanically known as *Hibiscus rosa-sinensis,* and hereinafter referred to by the name 'Scarlet Loke'.

The new *Hibiscus* is a product of a planned breeding program conducted by the Inventor in Alva, Fla. The objective of the breeding program is to create new freely-branching *Hibiscus* cultivars with a dense, uniform and compact plant habit appropriate for container production, early and uniform flowering, numerous flowers per lateral branch, desirable flower color and good garden performance.

The new *Hibiscus* originated from a cross-pollination made by the Inventor in Alva, Fla. in 1994, of a proprietary selection of *Hibiscus rosa-sinensis* identified as code number YB-602, not patented, as the female, or seed, parent with *Hibiscus rosa-sinensis* 'Island Fire', disclosed in U.S. Plan Pat. No. 7,378, as the male, or pollen, parent. The new *Hibiscus* was discovered and selected by the Inventor as a flowering plant within the progeny of the stated cross-pollination in a controlled greenhouse environment in Alva, Fla. on Sep. 5, 1995.

Asexual reproduction of the new *Hibiscus* by vegetative terminal cuttings in a controlled greenhouse environment in Alva, Fla. since February, 1996, has shown that the unique features of this new *Hibiscus* are stable and reproduced true to type in successive generations.

SUMMARY OF THE INVENTION

Plants of the new *Hibiscus* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Scarlet Loke'. These characteristics in combination distinguish 'Scarlet Loke' as a new and distinct cultivar of *Hibiscus:*

1. Compact, upright, somewhat outwardly spreading and dense plant habit that is appropriate for container production.
2. Glossy dark green-colored leaves.
3. Uniform, freely and early flowering habit.
4. Large scarlet red-colored flowers.
5. Good postproduction and garden performance.

Plants of the new *Hibiscus* can be compared to plants of the female parent selection. Plants of the new *Hibiscus* differ from plants of the female parent selection in the following characteristics:

1. Plants of the new *Hibiscus* are more vigorous than plants of the female parent selection.
2. Plants of the new *Hibiscus* are fuller and denser than plants of the female parent selection.
3. Plants of the new *Hibiscus* and the female parent selection differ in flower color as plants of female parent selection have light orange-colored flowers.

Plants of the new *Hibiscus* can be compared to plants of the male parent, 'Island Fire'. Plants of the new *Hibiscus* differ from plants of 'Island Fire' in the following characteristics:

1. Plants of the new *Hibiscus* are more freely flowering than plants of 'Island Fire'.
2. Plants of the new *Hibiscus* and 'Island Fire' in flower color as plants of 'Island Fire' have red-colored flowers.

Plants of the new *Hibiscus* can be compared to plants of the *Hibiscus rosa-sinensis* 'Baja Breeze', disclosed in U.S. Plant Pat. No. 17,607. In side-by-side comparisons conducted in Alva, Fla., plants of the new *Hibiscus* differed from plants of 'Baja Breeze' in the following characteristics:

1. Plants of the new *Hibiscus* were more vigorous than plants of 'Baja Breeze'.
2. Flowers of plants of the new *Hibiscus* and 'Baja Breeze' differed in flower color as plants of 'Baja Breeze' had red-colored flowers.

3. Plants of the new *Hibiscus* had better garden performance than plants of 'Baja Breeze'.

BRIEF DESCRIPTION OF THE PHOTOGRAPHS

The accompanying colored photographs illustrate the overall appearance of the new *Hibiscus,* showing the colors as true as it is reasonably possible to obtain in colored reproductions of this type. Colors in the photographs may differ slightly from the color values cited in the detailed botanical description which accurately describe the colors of the new *Hibiscus.*

The photograph at the bottom of the sheet comprises a side perspective view of typical flowering plants of 'Scarlet Loke' grown in a container.

The photograph at the top of the sheet comprises a close-up view of a typical flower of 'Scarlet Loke'.

DETAILED BOTANICAL DESCRIPTION

The aforementioned photographs and following observations, measurements and values describe plants grown in Bonsall, Calif. in one-gallon containers in polyethylene-covered greenhouses during the spring under conditions which closely approximate commercial production. During the production of the plants, day temperatures ranged from about 18° C. to about 38° C. and night temperatures ranged from about 16° C. to about 21° C. Plants had been growing for 18 weeks when the photographs and the description were taken. In the description, color references are made to The Royal Horticultural Society Colour Chart, 2001 Edition, except where general terms of ordinary dictionary significance are used.

Botanical classification: *Hibiscus rosa-sinensis* 'Scarlet Loke'.

Parentage:

*Female, or seed, parent.*—Proprietary selection of *Hibiscus rosa-sinensis* identified as code number YB-602, not patented.

*Male or pollen parent.*—*Hibiscus rosa-sinensis* 'Island Fire', disclosed in U.S. Plant Pat. No. 7,378.

Propagation:

*Type.*—By vegetative terminal cuttings.

*Time to initiate root.*—About 10 days at temperatures of 24° C.

*Time to develop roots.*—About four weeks at temperatures of 24° C.

*Root description.*—Thick, fibrous; white in color.

*Rooting habit.*—Moderate branching; moderately dense.

Plant description:

*Plant form and growth habit.*—Perennial, evergreen, upright, somewhat outwardly spreading and dense. Moderately vigorous growth habit.

*Branching habit.*—Freely branching, usually about six lateral branches develop.

*Plant height.*—About 38 cm.

*Plant diameter* (*area of spread*).—About 20 cm.

Lateral branch description:

*Length.*—About 7 cm.

*Diameter.*—About 3 mm.

*Internode length.*—About 2.6 cm.

*Texture.*—Immature sparsely pubescent; mature, woody and rough.

*Color, immature.*—Close to 146A.

*Color, mature.*—Close to 199A to 199B.

Foliage description:

*Arrangement.*—Alternate, single; numerous; symmetrical.

*Length.*—About 8.6 cm.

*Width.*—About 6.8 cm.

*Shape.*—Ovate.

*Apex.*—Acute.

*Base.*—Obtuse.

*Margin.*—Broadly serrate to crenate.

*Texture, upper and lower surfaces.*—Smooth, glabrous; leathery and tough.

*Luster, upper surface.*—Glossy.

*Luster, lower surface.*—Somewhat glossy.

*Venation pattern.*—Pinnate, arcuate.

*Color.*—Developing leaves, upper and lower surfaces: Close to 146A. Fully expanded leaves, upper surface: Close to N137A; venation, close to 147B. Fully expanded leaves, lower surface: Close to 146B; venation, close to 146C.

*Petiole.*—Length: About 3.2 cm. Diameter: About 3 mm. Texture, upper and lower surfaces: Slightly pubescent. Color, upper and lower surfaces: Close to 146B.

Flower description:

*Flower arrangement.*—Flowers arranged singly at terminal leaf axils. Uniform and freely flowering habit with usually about ten flower buds and/or open flowers per plant at one time. Flowers face upright to outwardly.

*Flower appearance.*—Rounded, scarlet red-colored flowers. Flowers are open for about two days. Flowers not persistent.

*Natural flowering season.*—Usually spring and summer or during periods of warm weather; plants flower year-round in the greenhouse.

*Flower diameter.*—About 8.7 cm.

*Flower length* (*height*).—About 8.2 cm.

*Flower bud.*—Resistance to abscission during shipping: Plants of the new *Hibiscus* have been observed to resist flower bud drop when stored in a closed box for five days at 13° C. Rate of opening: About four to five days depending on temperatures. Length: About 3 cm. Diameter: About 1.1 cm. Shape: Ovate. Color: Close to 53A.

*Petals.*—Arrangement: Corolla consists of five petals that are fused at base; petals imbricate. Length: About 7 cm. Width: About 5.2 cm. Shape: Obovate. Apex: Rounded. Base: Attenuate. Margin: Entire. Texture: Smooth, glabrous; velvety; veins prominent on the lower surface. Color: When opening, upper surface: Close to 42A. When opening, lower surface: Close to 43B. Fully opened, upper surface: Close to 44A; towards the base, close to 47B. Color does not fade with development. Fully opened, lower surface: Close to 45D. Color does not fade with development.

*Sepals.*—Appearance: Five sepals fused into a tubular star-shaped calyx. Length: About 1.4 cm. Width: About 8 mm. Shape: Elliptical. Apex: Acute. Margin: Entire. Texture, upper and lower surfaces: Slightly pubescent. Color, upper and lower surfaces: Close to 146B.

*Bracts.*—Appearance: About eight fused at base. Length: About 1 cm. Width: About 2 mm. Shape: Lanceolate. Apex: Acute. Margin: Entire. Texture, upper surface: Smooth, glabrous. Texture, lower surface: Sparsely pubescent. Color, upper and lower surfaces: Close to 146A.

*Peduncles.*—Length: About 6.1 cm. Diameter: About 2.5 mm. Angle: About 45° from the lateral branch axis. Strength: Strong, flexible. Texture: Sparsely pubescent. Color: Close to 146C.

*Reproductive organs.*—Androecium: Stamen number: Numerous, about 98. Filament length: About 4 mm. Filament color: Close to 50A. Anther shape: Oval. Anther length: About 1 mm. Anther color: Close to 9A. Amount of pollen: Scarce. Pollen color: Close to 13A. Gynoecium: Pistil length: About 9.2 cm. Style length: About 7.4 cm. Style texture: Smooth, waxy. Style color: Close to 158C. Stigma appearance: Five-parted, rounded. Stigma color: Close to 46A. Ovary color: Close to 158A.

*Seed/fruit.*—Seed and fruit production has not been observed.

Garden performance: Plants of the new *Hibiscus* have been observed to have good garden performance and to tolerate wind, rain and temperatures from about 0° C. to about 38° C.

Pathogen/pest resistance: Plants of the new *Hibiscus* grown under Florida production conditions have not been shown to be susceptible to pathogens common to *Hibiscus* such as Pseudomonas, Pythium and Phytophthora. Plants of the new *Hibiscus* have not been observed to be tolerant to pests and other pathogens.

It is claimed:

1. A new and distinct *Hibiscus* plant named 'Scarlet Loke' as illustrated and described.

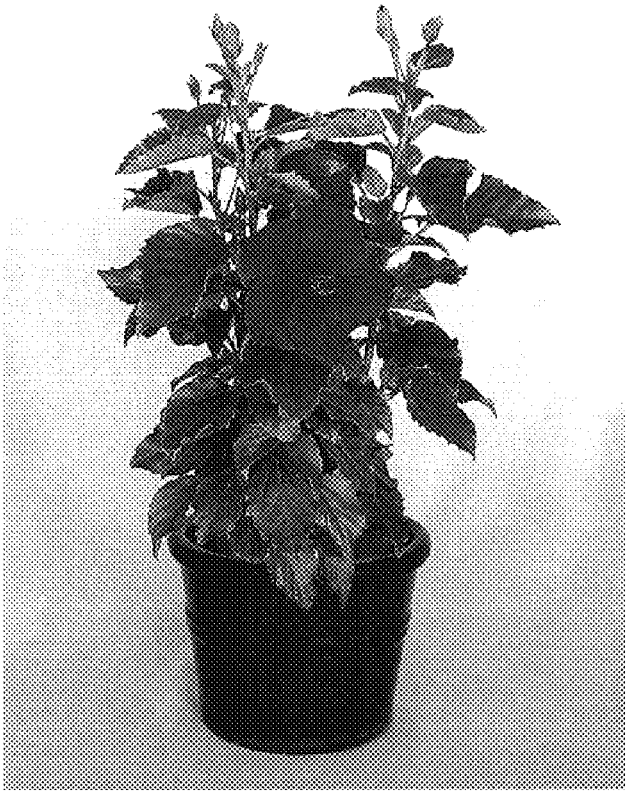
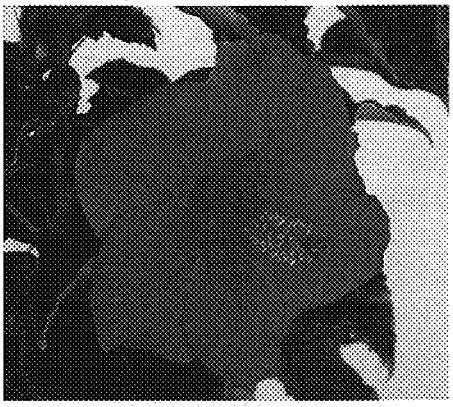

* * * * *